United States Patent [19]

Wacker et al.

[11] 4,139,611

[45] Feb. 13, 1979

[54] ORGANIC PEPTIDE CONTAINING SUBSTANCE RECOVERED FROM BLOOD HAVING INSULIN-LIKE ACTIVITY

[75] Inventors: Adolf Wacker; Dörthe Wacker, both of Neu-Isenburg; Klaus Pöhler, Wiesbaden; Hellmut Mittenzwei, Münich, all of Fed. Rep. of Germany

[73] Assignee: Helmut Mittenzweig, Munich, Fed. Rep. of Germany

[21] Appl. No.: 848,109

[22] Filed: Nov. 3, 1977

Related U.S. Application Data

[62] Division of Ser. No. 748,956, Dec. 9, 1976, Pat. No. 4,085,204.

[30] Foreign Application Priority Data

Dec. 24, 1975 [DE] Fed. Rep. of Germany ....... 2558537

[51] Int. Cl.$^2$ ..................... A61K 35/14; A61K 37/00; A61K 37/26
[52] U.S. Cl. .................................... 424/101; 424/177; 424/178
[58] Field of Search ....................... 424/178, 177, 101; 260/112 R

[56] References Cited

PUBLICATIONS

Bromer et al., Chem. Abst., vol. 66 (1967), p. 62234a.

*Primary Examiner*—Sam Rosen
*Attorney, Agent, or Firm*—Hammond & Littell

[57] ABSTRACT

Organic peptide containing substances with insulin-like activity derived from blood or a blood component of a warm-blooded animal, which comprises the steps of pre-treating the blood or blood component by adjusting the pH thereof to a value of from 2 to 4 or of from 8 to 10, incubating the pre-treated blood at a temperature of from about 15 to about 40° C. for a period of at least four hours, cooling the incubated blood to a temperature of less than 10° C., and recovering from the treated blood after neutralization organic peptide substances having a molecular weight of from about 1000 to about 5000, and an insulin-like activity of from about 14 to about 40 $\mu$U/mg solid.

4 Claims, No Drawings

ORGANIC PEPTIDE CONTAINING SUBSTANCE RECOVERED FROM BLOOD HAVING INSULIN-LIKE ACTIVITY

PRIOR APPLICATION

This application is a division of copending, commonly assigned U.S. patent application Ser. No. 748,956 filed Dec. 9, 1976, now U.S. Pat. No. 4,085,204.

This invention relates to a process for obtaining insulin-like active substances and to substances obtained by such process. More particularly, the invention relates to a process for recovering insulin-like active substances from one or more blood components of a warm blooded animal.

It is known that certain substances recovered from the blood of warm blooded animals possess a certain amount of insulin-like activity along with other activities such as respiration stimulating activity and growth regulating activity. Such an insulin-like activity is for example posessed by the products described in Arz. Forsch. 18, 1019 (1968) as well as in J. Cell. Physiol. 79, 319 (1972) which are products isolated by special procedures from the blood of warm blooded animals, preferably from blood or serum of calves.

It is an object of this invention to provide a process specifically directed to obtaining substances having insulin-like activity, or substances having a high proportion of insulin-like active compounds. Said insulin like active substances are, in accordance with the invention, recovered from blood components derived from warm blooded animals other than human, which is of considerable advantage both from an efficacy point of view and furthermore from a costs point of view. Thus, the insulin-like active substances isolated from the blood of warm blooded animals, preferably from one or more blood components derived from sexually immature calves, possess a quantitatively higher proportion of insulin-like active substances which activity is not inhibited by insulin antibodies present either in the human or animal system.

Whilst blood or serum having insulin-like activity only posesses an activity of 2.5 to 8 $\mu$U/mg solids content, it has now been found that by a particular treatment of blood or a blood component, a product can be recovered which has a high proportion of substances having insulin-like activity, namely an activity of from about 14 to about 40 $\mu$U/mg solids content.

The process in accordance with the invention for obtaining insulin-like active substances comprises the steps of pre-treating blood or a blood component by adjusting the pH thereof to a value of from 2 to 4, incubating the pre-treated blood at a temperature of from about 16° to about 40° C. for a period of a least four hours, cooling the incubated blood to a temperature of less than 10° C., and after neutralisation, recovering from the treated blood conponents organo-peptide containing insulin-like active substances having a molecular weight of from about 350 to 5000 and an insulin-like activity of from about 14 to about 40 $\mu$U/mg solid.

The process described above can be equally well effected by adjusting the pH of the blood or blood component to a value of from 8 to 10 and then following the procedure described above.

Prior to adjustment of the pH, the blood or blood component should be diluted with from about one half to about four volumes of a hydrophilic diluent.

The blood or blood component employed is normally whole blood, plasma, serum, erythrocyte suspension or thrombocyte suspension. However, the blood component may constitute the residue remaining after inorganic or organic substances of molecular weight less than about 5000 have been substantially removed from the blood or blood component. Similarly, the blood component may comprise the residue remaining after inorganic or organic substances of molecular weight less than about 1000 have been removed from the blood or blood component.

The procedure by which the insulin-like active substances may be recovered from the treated blood or blood component may preferably comprise dialysing such treated blood or blood component against a membrane adapted to pass molecules having a molecular weight of less than about 6,000, and recovering the insulin-like active substances from the dialysate.

The insulin-like active substances recovered by the process described above may be subjected to an insulin-like active enrichment process, in which inorganic salts and lower molecular weight substances are removed from the recovered insulin-like active substance to obtain an insulin-like active product having an insulin-like activity of from about 35 $\mu$U/mg to about 200 $\mu$U/mg solid.

It is recommended that the recovered insulin-like active substances or insulin-like active product be concentrated down or diluted to obtain an isotonic solution having a solids content of about 2.5 to 20 mg/ml with an insulin-like activity of about 500 $\mu$U/mg, where necessary by adjustment with glucose or sodium chloride.

The insulin-like active organo-peptide containing substances obtained from blood or a blood component of a warm-blooded animal have a molecular weight of from about 350 to 6000, a non-suppressible insulin-like activity in the rat adipose tissue test of from about 35 to 200 $\mu$U/mg solids, solubility in ethanol, stability to heat at neutral pH, a positive ninhydrin and amido black G-reaction, a UV maximum at 258 millimicrons indicating presence of purine derivatives, an amino acid content after hydrolysis providing a peptide content of from 25 to 30% of the dry weight of the salt free substances, with the following amino acids: Glutamic acid, Leucine, Glycine, Serine, Asparginic acid, Alanine, Isoleucine, Histidine, Valine, Threonine, Lysine, Methionine, Thyrosine, Proline and Arginine, an insulin-like activity indicated by uptake of glucose in adipose tissue, a blood sugar lowering effect in warm-blooded animals and an inhibition of lipolysis and the growth increase of cell cultures such as fibroblasts.

The insulin-like activity of the substances obtained by the process of the invention is determined using adipose tissue of rats in accordance with the method described in J. Clin. Invest. 39, 1487–1498 (1969). For each adipose tissue test, which consists of twenty-four individual tests, three male rats of a weight of about 180 to 200 g are employed. After preparation of the two epidymal adipose tissues, these are cut and so divided that each of 24 reaction flasks contains a forward, middle or rearward section of the adipose tissue (totalling 80–100 mg adipose tissue). Each determination is carried out in triplicate, in which 35 mg portions of the preparations on which insulin-like activity is to be determined is weighed out each time and dissolved in 7 ml of Krebs-Ringer bicarbonate buffer which contains 100 mg% gelatine and 250 mg% glucose. The insulin curve employed for guaging insulin-like activity covers a range of from 63 to 252 μU of insulin. The complete charges contain about 100 mg of adipose tissue, 9.5 mg of substance on which the insulin-like activity is to be determined (or also standard controls or different insulin concentrations), 1.9 ml Krebs-Ringer bicarbonate buffer and 0.1 ml glucose —1—$C^{14}$. The charges are incubated at 37° C. for 2 hours.

An amount of 0.4 ml hyamine is then injected into the reaction flask for the purpose of collecting $C^{14}O_2$ and the while maintaining a closed system 0.25 ml of a 2N sulpluric acid solution is introduced with the aid of a cannula to liberate the $C^{14}O_2$. After half an hour incubation of the individual reaction flasks at a temperature of 37° C., the hyamine is transferred from the absorption-acting synthetic material caps into synthetic material flasks, which serve as counter flasks and which are filled with 8 ml toluene scintillation solution. The scintillation solution employed consists of 4 g of 2,5-diphenyl-oxazole, 100 mg 1,4-bis-2-(4-methyl-5-phenyl-oxazolyl) benzene and one liter of toluene. The radioactivity is measured in a liquid scintillation spectro-meter.

When the same test is carried out with the addition of insulin antibodies, there is no lowering or only a slight lowering of the measured values.

The determination of a stimulation or inhibition of lipolysis in adipose tissue is carried out by employing adipose tissue in which a lipolysis is induced with 0.4 μg adrenaline/ml or 0.1 μg/ml of glucagon. The concentration changes of the free fatty acids and glycerine is then determined in the medium before and after incubation with various concentrations of the substance whose insulin-like activity is to be tested. An insulin comparison curve is produced with insulin solutions of different concentrations between 1 and 100 μU/ml. The test method employed is described in detail in Arz. Forsch. 18, 1019 (1968).

The activity of the substances produced in accordance with the invention on the blood sugar level is also obtained in in vivo tests. In this test, Wistar rats having a weight of 250 g are injected intravenously with 3 g of glucose/kg. A comparison group, at the same time as the glucose injection, receives 2 mg of the substance of the invention obtained in the Example 4 (15 to 20 μU/mg). The blood sugar level in the control animals increases within 15 minutes up to 400 mg% and normalises again after 60 minutes to about 120 mg%. In the test animals treated with the active substances of the invention, a 20% lower blood sugar level is observed in the same time period.

Injection of the same substance of the invention in Alloxan-diabetic rats leads to a statistically significant blood sugar decrease in comparison with Alloxan-diabetic animals injected intravenously with the same amount of physiological salt solution in place of the substance of the invention.

The insulin-like active substances obtained in accordance with the process of the invention are useful blood sugar lowering agents in warm blooded animals in hyperglycemic condition, as for example specifically indicated by results obtained in the in vivo tests carried out on hyperglycemic rats described above. For this use, satisfactory results are obtained at daily dosages of from about 200 μU to about 500 μU/kg animal body weight, conveniently administered in divided doses two to three times a day. The preferred means of administration is by intravenous infusion, and the product of the invention is accordingly most conveniently provided in injectable liquid form.

A specific advantageous use of the insulin-like active products of the invention is as a supplement to regular insulin treatment of diabetic patients exhibiting the common ulceration side effects following on long term treatment with insulin. The advantage of said supplementary treatment is firstly attributed to the greater proportions of insulin-like active substances which are not suppressible by insulin antibodies, present in the substances recovered by the process in accordance with the invention, and secondly by virtue of growth regulating properties promoting healing which are present in said substances.

The influence of the pH value on the amount of insulin-like active substance obtained can be seen from the following Table. It will be noted that at the pH ranges of 2 to 4 or 8 to 10 chosen in the process of the invention as against other pH values, a particularly high total yield of substances having insulin-like activity is obtained.

Table
Influence of pH value on the recovery of substances having insulin-like activity

| Mean pH value | Yield in g dry weight/100 ml | Insulin-like activity μU/mg | Total insulin-like activity mU |
|---|---|---|---|
| Blood pH 7 | 1,2 | 11,0 | 13,2 |
| pH 2,5 – 3,5 | 1,6 | 15,3 | 24,4 |
| pH 9 – 10 | 1,3 | 18,6 | 24,1 |
| Plasma pH 7 | 1,8 | 6,5 | 11,7 |
| pH 2,5 – 3,5 | 2,7 | 14,7 | 39,7 |
| pH 9 – 10 | 1,9 | 8,6 | 16,3 |
| Erythrocyte sediment (1:1) | | | |
| pH 7 | 0,9 | 9,0 | 8,1 |
| pH 2,5 – 3,5 | 2,8 | 5,3 | 14,8 |
| pH 9 – 10 | 1,4 | 14,3 | 20,0 |
| Pre-dialysed blood | | | |
| pH 7 | 0,3 | 16,0 | 5,0 |
| pH 3 | 3,0 | 15,0 | 30,0 |
| pH 9,5 | 3,5 | 30,0 | 90,0 |

EXAMPLE 1

Three liters of fresh blood taken from slaughter calves is mechanically mixed with 300 ml of a 3.8% sodium citrate solution and 20 g of phenol and cooled to 4° C. After dilution with 900 ml of demineralised water, the pH is adjusted to 3.5 by the addition of about 100 ml of 6N hydrochloric acid. The mixture is then warmed with stirring for 24 hours to 35° to 40° C. Cooling to 4° C. is then again effected and the whole is then dialysed in membrane tubes allowing for passage of molecules up to about 500 to 6000 Dalton against distilled water comprising 0.2% phenol. The ratio of inner to outer dialysate is about 1:5 to about 1:10. The membrane tubes are mechanically agitated to optimise the dialysis effect. After 24 hours, the dialysate is renewed, and after a further 24 hours this renewal is repeated. The inner dialysate may be worked up further in accordance with Example 4. The combined outer dialysates are concentrated down to 2 liters in a vacuum concentrator at a maximum temperature of 35° C. and the pH adjusted to 7.0 with 2N ammonia solution. The solution is then again concentrated to 2 liters volume, possible precipitates centrifuged off, and the clear solution freeze-dried. One obtains 48 g of a substance mixture (dry) having an insulin-like activity of 15.3 μU/mg.

EXAMPLE 2

The citrate-containing fresh calf blood (3 liters) described in Example 1 is filled into centrifuge flasks up to 500 ml and centrifuged at 4° C. in a Christ centrifuge, model 4 KS, for 30 minutes at 3,400 revolutions per minute. From 1 liter of blood, one obtains 0.6 to 0.75 liters of remaining plasma, which is pipetted off and collected. The erythrocyte sediment (0.30 to 0.45 liter) is diluted at a ratio of 1:1 with aqueous 0.5% phenol and also collected for further treatment (see Example 3). One liter of the plasma portion is diluted with distilled water containing 0.5% phenol and the pH adjusted to 3.0 with 6N hydrochloric acid. The further heat treatment, dialysis, concentration and lyophilisation is carried out in a manner analogous to Example 1. From one liter of plasma, 27 g of dry substance having an insulin-like activity of 14.7 $\mu$U/mg is obtained.

EXAMPLE 3

The erythrocyte suspension obtained from 3 liters of calf blood in accordance with Example 2 is adjusted to a pH of 9.0 with 5N ammonia solution and treated with 200 to 300 ml ethanol to lower its viscosity. The erythrocytes Haemolise. After centrifuging, a clear solution is obtained. Heat treatment, and three dialyses, concentration and neutralisation with hydrochloric acid of the collected outer dialysates in then carried out with following lyophilisation in accordance with Example 1. From 1 liter of 1:1 erythrocyte suspension 14 g of dry substance is obtained with an insulin-like activity of 14.3 $\mu$U/mg.

EXAMPLE 4

The process described in Examples 1 to 3 is repeated, in which however the inner dialysate obtained by dialysis of blood or a blood component at neutral pH value is employed as starting material. For this purpose 100 liters of a neutral inner dialysate (blood, plasma or erythrocyte suspension 1:1) is adjusted to a pH value of 3.5 with 6N hydrochloric acid while sirring. The resulting material is then treated with 100 liters of 50% by volume ethanol to lower its viscosity, and this is then incubated for 24 to 48 hours with stirring at 20° to 30° C., with protection of 0.5% phenol solution. After cooling to 4° C. the 200 liters of solution is again dialysed against a 0.2% aqueous phenol solution. A strong swelling of the inner dialysate takes place which can be kept within limits by stirring. The ratio of the volume of inner dialysate to outer dialysate lies between 1:2 to 1:5. After every 24 hours, the outer dialysate is renewed. The collected outer dialysates (about 2,200 liters at a pH of 3.5) is concentrated down to 25 liters under vacuum, neutralised with 5N ammonia solution, cloudiness filtered off and further concentrated to 3.5 liters. The solution is then allowed to stand for one week at 4° C., precipitate filtered off and the remaining solution lyophilised after correction of the pH to value of 6.9 to 7.0. From 100 liters of inner dialysate (corresponding to about 85 liters of blood) one obtains about 350 g of dry substance having an insulin-like activity of 15 to 20 $\mu$U/mg.

EXAMPLE 5

The process described in Example 4 is repeated, in which however the starting material employed as inner dialysate for recovering insulin-like active substances is incubated and dialysed in the same way at a pH of about 9.5. The outer dialysate thus obtained is then neutralised with hydrochloric acid or acetic acid. In this process one obtains from 100 liters of blood inner dialysate about 350 g of dry substance having an insulin-like activity of 30 to 40 $\mu$U/mg.

EXAMPLE 6

Ten liters of freshly taken calf or swine blood is mechanically mixed with 100 ml of a 3.8% sodium citrate solution and 60 g of phenol in accordance with Example 1, cooled to 4° C. and diluted with 2 liters of demineralised water. The resulting solution is firstly clarified with the aid of a centrifuge and then filtered through an ultrafiltration membrane (e.g. PSAC-Pellicon membranes of acetylcellulose) having a permeability up to 100 Dalton at 6 atmospheres pressure. In this manner, inorganic and organic components having a molecular weight of less than about 800 to 1200 Dalton are eliminated and a thick viscous paste remains which is taken up in 2 liters of distilled water. The suspension thus obtained is then treated in accordance with Example 1, 2 or 3 by acidifying or rendering alkaline and dialysing. The outer dialysate after collection, neutralisation, concentration and lyophilising so obtained contains 25 to 30 g of dry substance having an insulin-like activity of 20 to 30 $\mu$U/mg.

EXAMPLE 7

4.5 g of the product obtained in accordance with Example 4 having an insulin-like activity of 15 to 20 $\mu$U/mg is dissolved in 25 ml distilled water. The solution is transferred to a column (50 × 100) containing a strongly cross-linked dextran gel having a fractionating range of up to 700 Dalton (e.g. Sephadex 10, 40 to 120 $\mu$m cross-section). The column is then eluted with 0.1N acetic acid at a rate of 60 ml/hour. Fractions each of 12.4 ml are collected which are measured for UV absorption at 206 and 254 millimicrons in a UV absorption photometer (e.g. Uvicord III), whereby three main peaks are obtained (fractions numbered 49 to 79; 80 to 119 and 120 to 540). The main proportion of the inactive salts are found in fraction II. The fraction I, with a yield of 115 mg contains the main proportion of salt free substance having an insulin-like activity of 60 $\mu$U/mg. The fraction III contains mainly low molecular weight inactive organic substances. The molecular weight determination of the substance (115 mg) from fraction I is carried out on a calibrated gel filtration column (26 × 100) containing cross-linked dextran gel (e.g. Sephadex 25, medium 50 to 150 $\mu$m cross-section). The elution with 1N acetic acid (16 ml/hour) shows a main proportion of about 99% substance having a molecular weight of less than 1000 Dalton, the previous fraction (15 mg, i.e. 7.2% of the total organic content of the fraction) lies in the region between 350 and 5,000 Dalton and shows the total insulin-like active activity of 150 $\mu$U/mg.

EXAMPLE 8

3 g of the product obtained according to Example 1 having an insulin-like activity of 15.3 $\mu$U/mg dissolved in 15 ml of water are transferred within 5 hours into a Hanish electrophoresis apparatus which allows for fractionating into 90 fractions. The solution is diluted 1:1 with chamber buffer which consists of a 1:3 diluted electrode buffer. The electrode buffer of a pH of 4.9 employed is a mixture of 100 ml pyridine and 80 ml glacial acetic acid which is diluted to 9000 ml with water. The electrophoresis is carried out at a potential of 1800 to 1500 volts and a current of from 150 to 165 mA at a temperature of 5° C. The buffer pump pumps 10 ml/hour and the dosing pump 1.5 ml/hour, and thus 0.75 ml of the active solution. Nine fractions are separated, in which the fraction 6 (tubes 41 to 44), fraction 7 (tubes 45 to 48) and fraction 9 (tubes 53 to 55) show insulin-like activity. These fractions are lyophilised. Fraction 6 provides 16 mg substance having an insulin-like activity of 60 µU/mg, fraction 7 provides 12.8 mg having an insulin-like activity of 150 µU/mg and fraction 9 provides 9.6 mg having an insulin-like activity of 190 µU/mg. All three fractions show a positive ninhydrin and amido black G-reaction.

EXAMPLE 9

4 g of the product obtained in accordance with Example 3 having an insulin-like activity of 14.3 µU/mg are dissolved in 100 ml of distilled water, are transferred to a column (26 × 40) containg a cation exchanger based on a polystyrene matrix (e.g. AG 50 W-x8) which is available in $NH_4$-form and has a particle size of from 75 to 150 µm. After soaking in of the test solution, the column is washed with distilled water until no substance is shown to exist in the eluate (about 2 liters) by means of an UV spectro-photometer (wave length 254 millimicrons). This eluate is discarded. The column is successively eluted with 200 ml of a 10% ammonia solution and 3 liters of distilled water. The collected eluate is concentrated under vacuum to one fifth of its original volume and then freeze-dried. 550 mg of salt-free lyophilisate is thus obtained with an insulin-like activity of 32 µU/mg. An amino acid analysis of the fraction I obtained in Example 7 shows, before and after hydrolysis (under nitrogen with 6N hydrochloric acid at a temperature of 110° C. over a time period of 24 hours), the following values in percent: Ornithine und Lysine (12,23; 22,25), Histidine (1,30; 2,89), Arginine (traces; 0,47), Asparagine acid (0,71; 2,42), Threonine (0,61; 1,13), Serine (0.39; 1,85), Glutaminic acid (0,20; 2,16), Proline (1,38; 1,93), Glycine (0,15; 1,35), Alanine (1,54; 3,99), Cysteine (0,06; 0,08), Valine (1,12; 2,41), Methionine (0,17; 0,25), Isoleucine (0,14; 0,36), Leucine (0,16; 1,67), Tyrosine (0,52; 1,15) and Phenylalanine (Traces; 0,10).

What we claim is:

1. An organic peptide containing substance having insulin-like activity recovered from blood or a blood component of a warm-blooded animal, obtain by the steps of pretreating the blood or blood component by diluting the blood or blood component with from about half to about four volumes of a hydrophilic diluent, adjusting the pH of the resulting solution to a value of from 2 to 4 or of from 8 to 10, incubating the pretreated blood at a temperature of from about 15° to about 40° C. for a period of at least four hours, cooling the incubated blood to a temperature of less than 10° C., dialysing the treated blood after neutralization against a membrane adapted to pass molecules having a molecular weight of less than 6000, and recovering from dialysate organic peptide substances having a molecular weight of from about 350 to about 6000, and an insulin-like activity of from about 14 to about 40 µU/mg solid.

2. An organic peptide containing substance of claim 1 recovered from blood or a blood component of a warm-blooded animal, having a molecular weight of from about 350 to 6,000, a non-suppressible insulin-like activity in the rat adipose tissue test of from about 35 to 2000 µU/mg solids, solubility in ethanol, stability to heat at neutral pH, a positive ninhydrin and amido black G-reaction, an UV maximum at 258 millimicrons indicating presence of purine derivatives, an amino acid content after hydrolysis providing a peptide content of from 25 to 30% of the dry weight of the salt free substance, with the following amino acids: Glutamic acid, Leucine, Glycine, Serine, Asparginic acid, Alanine, Isoleucine, Histidine, Valine, Threonine, Lysine, Methionine, Tyrosine, Proline and Arginine, an insulin like activity indicated by uptake of glucose in adipose tissue, a blood sugar lowering effect in warm-blooded animals, and an inhibition of lypolysis and the growth increase of cell cultures.

3. A peptide of claim 1 wherein the recovered insulin-like active substance is adjusted to obtain an isotonic solution having a solids content of from about 2.5 to about 20 mg/ml, and if necessary to obtain the isotonic solution, adding glucose or sodium chloride.

4. A peptide of claim 1 wherein the recovered insulin-like active substance is adjusted to possess an insulin-like activity of about 500 µU/ml and, if necessary to obtain an isotonic solution, adding glucose or sodium chloride.

* * * * *